United States Patent [19]

Duisters et al.

[11] Patent Number: 5,545,789
[45] Date of Patent: Aug. 13, 1996

[54] PROCESS FOR THE DIMERIZATION OF A CONJUGATED DIENE

[75] Inventors: Henricus A. M. Duisters, Budel, Netherlands; Johan G.D. Haenen, Hasselt, Belgium

[73] Assignee: DSM N.V., Heerlen, Netherlands

[21] Appl. No.: 435,328

[22] Filed: May 5, 1995

Related U.S. Application Data

[63] Continuation of PCT/NL93/00211, Oct. 21, 1993.

[30] Foreign Application Priority Data

Nov. 5, 1992 [NL] Netherlands ............... 9201931

[51] Int. Cl.$^6$ ................ C07C 2/52; C07C 2/20
[52] U.S. Cl. ............ 585/508; 585/510; 585/514; 585/531; 585/527; 585/528; 585/369; 585/361
[58] Field of Search ................ 585/508, 510, 585/514, 531, 527, 528, 369, 361

[56] References Cited

U.S. PATENT DOCUMENTS

| | | |
|---|---|---|
| 3,655,793 | 4/1972 | Myers . |
| 4,144,278 | 3/1979 | Strope . |
| 4,181,707 | 1/1980 | Strope . |

*Primary Examiner*—Asok Pal
*Assistant Examiner*—Bekir L. Yildirim
*Attorney, Agent, or Firm*—Cushman, Darby & Cushman, L.L.P.

[57] ABSTRACT

The invention relates to a process for the dimerization of a conjugated diene using an iron triad metal nitrosyl halide, in combination with a reducing agent, as catalyst. The process is characterized in that the dimerization is carried out in the presence of nitrogen monoxide (NO). The invention is of interest in particular for the dimerization of butadiene to 4-vinyl cyclohexene.

31 Claims, No Drawings

PROCESS FOR THE DIMERIZATION OF A CONJUGATED DIENE

RELATED APPLICATIONS

This application is a continuation of PCT/NL93/00211 filed Oct. 21, 1993.

FIELD OF THE INVENTION

The invention relates to a process for the dimerization of a conjugated diene using an iron triad metal nitrosyl halide, wherein the halide is either chlorine, bromine or iodine, in combination with a reducing agent, as catalyst.

BACKGROUND OF THE INVENTION

Such a process is known from U.S. Pat. No. 4,144,278. In this known process a conjugated diolefin (or conjugated diene) is dimerized by the effect of a nitrosyl metal halide. The metal to be used is an iron triad metal, which here and hereinafter is understood to be a metal from the group formed by iron, cobalt and nickel.

Applicant has found that, when carrying out such a process, with time an unacceptable reduction of the catalytic activity occurs. This reduction is manifested in at least two ways:
1) The catalytic activity of the catalyst decreases upon storage. A freshly prepared nitrosyl metal halide catalyst has a higher activity (to be expressed in moles of converted diene per mole of catalyst and per unit of time) than a similar catalyst prepared already some time before use.
2) The catalytic activity also decreases during dimerization. Differential measurements proved that the activity is tending downwards.

SUMMARY AND OBJECTS OF THE INVENTION

The invention provides a solution to these problems and is characterized in that the reaction is carried out in the presence of nitrogen monoxide (NO). This is also understood to mean the use of compounds that release NO under reaction conditions (such as an alkali metal nitrite or ammonium nitrite). This ensures, on the one hand, that an aged catalyst (from storage) has its full, original activity, while on the other hand the catalytic activity is retained for a long time during dimerization. Retention of the original activity of the catalyst during the storage period in itself can also be achieved by keeping the catalyst under an NO atmosphere.

DETAILED DESCRIPTION OF THE INVENTION

The present invention relates to a process for the dimerization of a conjugated diene using an iron triad metal nitrosyl halide, in combination with a reducing agent. The dimerization is carried out in the presence of added nitrogen monoxide (NO). The process is of particular interest for the dimerization of butadiene to 4-vinyl cyclohexene.

In particular, a molar amount of NO is 1–1000 mol % of the stoichiometric amount of NO present in the catalyst; preferably, the molar amount of 10–250 mol %.

The catalyst to be used in the invention is an iron triad metal nitrosyl halide, the metal being iron, cobalt or nickel. Such halides have the following formula:

$[Fe(NO)_2X]_y$, $[Co(NO)_2X]_y$, $[Ni(NO)X]_y$ where
X=halogen (Cl, Br or I)
y=1 or 2 for Co and Fe =1, 2, 3 or 4 for Ni.

Such halides can be obtained by reaction of the metal halide with an NO or an NO source in the presence of the corresponding elemental iron triad metal.

Preferably, the catalyst also contains a ligand, so that the formula of the halide is: $Fe(NO)_2(L)X$, $Ni(NO)(L)X$ or $Co(NO)_2(L)X$, where L is a compound that is suitable to act as a ligand with the iron triad metal. Examples can be found in the patent already referred to, U.S. Pat. No. 4,144,278; they include phosphines, phosphine oxides, phosphites, arsines, arsonites, sulphides or stibonites.

The reducing agent can be chosen from the group formed by Grignard reagents (RMgX), organo-alkali metal compounds (RM), elemental zinc or nickel, zinc and cadmium organometals ($R_2Zn$ and $R_2Cd$) and organo-aluminium compounds (such as $R_2AlOR$ and $AlR_3$). In the above, M stands for an alkali metal, chosen from group 1 of the Periodic Table, and each R represents, independently, a hydrocarbyl group having, in general, from 1–20 C-atoms. More information on the use of reducing agents can be found in U.S. Pat. No. 3,377,397, in particular in column 2, lines 13–56. The reducing agent is preferably elemental zinc.

Optionally, also an activator can be added to the catalytic system, in the form of ethers, stibines, phosphines, phosphine oxides and heterocyclic sulphur or nitrogen compounds. For these, too, the reader is referred to U.S. Pat. No. 3,377,397, column 2, lines 58 ff.

We have found that when Zn powder is used during preparation of the catalyst, the iron triad metal nitrosyl halide is deposited on the finely divided Zn, so that in fact a heterogeneous catalyst is formed. It has been found that filtering off of the Zn used, after preparation of the catalyst, has virtually entirely removed the catalytic activity from the residual liquid. This also applies to the situation in which the corresponding elemental iron triad metal is present during preparation of the catalyst. This makes it possible to separate the reaction liquid and the catalyst after dimerization and reuse the latter.

The process according to the invention relates to the dimerization of a conjugated diene. Examples of such a diene include isoprene, 1,3-butadiene, 1,3-hexadiene, piperylenes, norbornadiene, 2,4-octadiene. Generally speaking, the process is suitable for conjugated diolefins with 4–20 carbon atoms per molecule. Mixtures of such dienes can also be dimerized in accordance with the process of the invention.

To prevent polymerization of the diene (or the dienes), the temperature at which dimerization is carried out must be between 0° and 150° C., preferably between 25° and 95° C. At higher temperatures polymerization of the diene will come to play an ever bigger part.

The dimerization can be carried out both in the presence and in the absence of a solvent. Examples of solvents are alkanes, aromatic compounds and ethers, such as, for instance, hexane, heptane, benzene, toluene, tetrahydrofuran and the like.

The pressure at which the reaction is carried out is not critical. What is important, though, is that the NO added during the reaction is also present in the liquid phase to a sufficient extent to have effective influence on the catalyst. Pressures of 0.1–10 MPa are, therefore, very suitable for carrying out the process according to the invention.

Besides the use of NO during the reaction, it has also been found to be advantageous to have an excess in the reaction medium of a compound forming a ligand with the catalyst, specifically a ligand as indicated and described in the above.

In principle this ligand-forming compound will be the same as the one already present in the catalyst system. There may be advantage, though, in having another ligand-forming compound present than the one originally present in the fresh catalyst so as to be able to influence the catalytic activity of the iron triad metal nitrosyl halide that way. One skilled in the art can easily find this out experimentally.

The reaction can be a batch reaction or a semi-batch reaction as well as a continuous reaction and will, generally speaking, take place in a stirred reactor. Upon completion of the reaction, which under the said process conditions yields a high selectivity and a high conversion, the resulting dimerization product can be separated off from the reactor stream in a manner known per se, for instance by distillation, absorption, etc.

Preferably, the process is applied to a feed stream containing butadiene or to the so-called $C_4$ raffinate fraction obtained during processing of the reaction product of the cracking process of hydrocarbon streams (such as catalytic cracking, steam or hydrocracking). Butadiene from the feed stream is then converted in the dimerization process to 4-vinyl cyclohexene, which can serve as raw material for the preparation of styrene.

The amount of catalyst that is used is generally $5*10^{-6}$ to $5*10^{-2}$ moles of halide per mole of diene to be dimerized.

Since the catalyst is sensitive to both oxygen and water, it is advisable that care is taken to ensure that the reaction takes place in the (virtual) absence of such components.

The invention will be elucidated on the basis of the following examples and comparative experiments; however, these are not meant to limit the invention.

Example I

Iron trichloride (0.1 mole of $FeCl_3$ or 16.2 grams of $FeCl_3$) and an excess of metallic iron (0.3 moles of Fe or 16.8 grams of Fe) were intensively stirred under nitrogen in THF (tetrahydrofuran; 300 ml) at reflux temperature (65° C.) in a glass flask until the colour changed from orange to grey.

Subsequently, nitrogen monoxide was passed through at a flow rate of 10 $Nlh^{-1}$ for 1 hour and then for another 2.5 hours at 5 $Nlh^{-1}$. During NO absorption the colour of the reaction mixture changed from grey to reddish brown. The end of $Fe(NO)_2Cl$ synthesis was marked by the appearance of brown $NO_x$ vapours. After cooling, the reaction mixture was filtered off under $N_2$, drawn off to remove the excess Fe and collected in an Erlenmeyer in an ice bath. The $Fe(NO)_2Cl$ synthesis efficiency was 90%, based on the N content and the Cl content.

Example II

The catalyst synthesis as described in Example I was carried out in the presence of the ligand-forming compound triphenyl phosphine (0.1 mole or 26.5 grams of $(C_6H_5)_3P$). The catalyst synthesis efficiency was 91%, based on the N content and the Cl content.

Example III

The catalyst synthesis as described in Example I was carried out in the presence of the ligand-forming compound triphenyl phosphine oxide (0.1 mole or 31.0 grams of $(C_6H_5)_3PO$). The catalyst synthesis efficiency was 88%, based on the N content and the Cl content.

Examples IV–VI and comparative experiments A–B

In batchwise dimerizations of 1,3-butadiene first 0.1 gram of metallic zinc (10-fold stoichiometric excess relative to the iron triad metal nitrosyl halide) was introduced into a 180 ml autoclave. After inertization using nitrogen 86.3 grams of 1,3-butadiene was pumped into the autoclave, after which the reaction temperature was set at 80° C. The initial pressure was determined by the vapour pressure of butadiene (about 1.2 MPa at 80° C.) and decreased at increasing butadiene conversion. After this, the catalyst solution was dosed, i.e. 2 ml of tetrahydrofuran (THF) in which 0.29 mmol catalyst (the halide) was present. From the introduction of the THF solution into the reactor activation (reduction) and subsequently dimerization took place. At the end of the dimerization reaction (at a pressure of 0.2 MPa) the 1,3-butadiene conversion and the selectivity to 4-vinyl cyclohexene were determined by means of gas chromatographic analysis.

Comparative experiment A

Freshly prepared $Fe(NO)_2Cl$ catalyst

Dosing of a freshly prepared Fe(NO)2Cl-THF solution, obtained in Example I, resulted in a transfer rate TR of 1330 $h^{-1}$ (TR=number of moles of dimer (here 4-vinyl cyclohexene) formed per mole of catalyst per unit of time).

Comparative experiment B

Aged $Fe(NO)_2Cl$ catalyst

The use of an aged $Fe(NO)_2Cl$-THF catalyst, i.e. after storage of the catalyst of Example I for 3 weeks at 0° C. under $N_2$, resulted in a TR of 800 $h^{-1}$.

Example IV

NO make-up during the dimerization reaction

After dosing of a fresh $Fe(NO)_2Cl$-THF solution, obtained in Example I, NO was dosed continuously to the batch reactor at a flow rate of $8.7*10^{-2}$ $Nlh^{-1}$ of NO during 90 minutes, or a total of 5.8 mmol of NO (10-fold excess relative to NO present in $Fe(NO)_2Cl$). A transfer rate TR of 1700 $h^{-1}$ was obtained.

Example V

Freshly prepared $Fe(NO)_2(Ph_3P)Cl$ catalyst with NO make-up

After dosing of a fresh Fe(NO)2(Ph$_3$P)Cl-THF solution, obtained in Example II, NO was dosed continuously to the batch reactor at a flow rate of $8.7*10^{-2}$ $Nlh^{-1}$ of NO during 90 minutes. A transfer rate TR of 1750 $h^{-1}$ was obtained.

Example VI

Freshly prepared $Fe(NO)_2(Ph_3PO)Cl$ catalyst with NO make-up

After dosing of a fresh Fe(NO)2(Ph$_3$PO)Cl-THF solution, obtained in Example III, NO was dosed continuously to the batch reactor at a flow rate of $8.7*10^{-2}$ $Nlh^{-1}$ of NO during 90 minutes. A transfer rate TR of 1600 $h^{-1}$ was obtained.

In all above examples and experiments the selectivity to 4-vinyl cyclohexene was 100%.

Example VII

The cyclodimerization of 1,3-butadiene was carried out continuously in a stirred reactor with an effective volume of 1.9 l. The continuous experiments were carried out at 90° C. in the liquid phase, a pressure of 0.5 MPa and a speed of 800 rpm.

1,3-Butadiene was fed at a flow rate of 1 kgh$^{-1}$ and metallic Zn powder at 1.3 g h$^{-1}$ (20-fold stoichiometric excess relative to the catalyst). Every four hours the 1,3-butadiene content and the 4-vinyl cyclohexene content were determined gas chromatographically.

A freshly prepared Fe(NO)$_2$Cl-THF solution (viz. a 4 wt. % solution of Fe(NO)$_2$Cl in THF prepared according to Example I) was fed to the reactor at a flow rate of 9 ml of THF h$^{-1}$ (0.03 wt. % Fe(NO)$_2$ Cl relative to the butadiene feed). Simultaneously, NO was introduced into the stirred reactor at a flow rate of 0.44 Nlh$^{-1}$ of NO (5-fold excess relative to NO present in Fe(NO)$_2$Cl). An average transfer rate TR of 3900 h$^{-1}$ over a period of 5 days was obtained. The selectivity to 4-vinyl cyclohexene was 100%.

What we claim is:

1. A process for the dimerization of a conjugated diene using an iron triad metal nitrosyl halide, wherein the halide is either chlorine, bromine or iodine, in combination with a reducing agent, as catalyst, wherein the dimerization is carried out in the presence of added nitrogen monoxide (NO).

2. The process acording to claim 1, wherein the NO is present during the dimerization in an amount of 1–1000 mol %, relative to the stoichiometric amount of NO in the catalyst.

3. The process according to claim 1 or 2, wherein said conjugated diene is butadiene which is dimerized to 4-vinyl cyclohexene.

4. The process according to claim 1 or 2, wherein said catalyst is a iron nitrosyl halide which is ligand-containing or nonligand-containing.

5. The process according to claim 1 or 2, wherein the dimerization is carried out in the presence of an excess of a compound forming a ligand with the catalyst.

6. The process according to claim 1 or 2, wherein said dimerization is conducted at a temperature between 25° and 95° C.

7. The process according to claim 1, wherein the molar amount of NO added is 10–250 mol % relative to the amount of NO in the catalyst.

8. The process according to claim 1 or 2, wherein the reducing agent comprises elemental zinc.

9. The process according to claim 1 or 2, wherein the catalyst contains a ligand.

10. The process according to claim 1 or 2, wherein the catalyst contains a ligand, said dimerization is conducted at a temperature between 25° and 95° C. and said reducing agent comprises elemental zinc.

11. A process for dimerizing a conjugated diolefin having 4–20 carbon atoms at a temperature between 0° C. and 150° C. in the presence of added nitrogen monoxide with an iron triad metal nitrosyl halide, wherein the halide is chlorine, bromine or iodine, in combination with a reducing agent, as catalyst.

12. The process according to claim 11, wherein said process is conducted under a pressure of 0.1 to 10 MPa.

13. The process according to claim 11, wherein the reducing agent is a Grignard reagent, an organo-alkali metal compound, an organo-aluminum compound, an organo-zinc compound, or an organo-cadmium compound.

14. The method according to claim 11, wherein the reducing agent comprises finely divided zinc or nickel.

15. The process according to claim 11, wherein the nitrogen monoxide is added in a molar amount of 1 to 1000 mol % relative to the amount of nitrogen monoxide present in said catalyst.

16. The process according to claim 11, wherein the molar amount of added nitrogen monoxide is 10 to 250 mol % relative to the amount of nitrogen monoxide present in said catalyst.

17. The process according to claim 11, wherein the dimerization is conducted at a temperature between 25° C. and 95° C.

18. The process according to claim 11, wherein the molar amount of added nitrogen monoxide is 1 to 1000 mol % relative to the amount of nitrogen monoxide present in said catalyst and the dimerization is conducted at a temperature between 25° C. and 95° C.

19. The process according to claim 18, wherein said reducing agent comprises elemental zinc.

20. The process according to claim 18, wherein the molar amount of added nitrogen monoxide is 10 to 250 mol % relative to the amount of nitrogen monoxide present in said catalyst.

21. The process according to claim 11, wherein said reducing agent is finely divided elemental zinc, said catalyst is an iron nitrosyl halide which optionally is ligand-containing, and the molar amount of added NO is 1–1000 mol % relative to the amount of NO in the catalyst.

22. The process according to claim 21, wherein the molar amount of added nitrogen monoxide is 10 to 250 mol % relative to the amount of nitrogen monoxide present in said catalyst.

23. The process according to claim 21, wherein the dimerization is conducted at a temperature between 25° C. and 95° C.

24. The process according to claim 11, wherein the catalyst is an iron nitrosyl halide, said catalyst optionally being a ligand-containing catalyst.

25. The process according to claim 11, wherein said process is conducted in the presence of an excess of a compound forming a ligand with the catalyst.

26. The process according to claim 11, wherein said catalyst is an iron nitrosyl chloride catalyst.

27. A process for dimerizing a conjugated diolefin which comprises subjecting a feed stream containing butadiene to a temperature between 0° C. and 150° C. in the presence of an iron triad metal nitrosyl halide which may optionally be ligand-containing, wherein the halide is chlorine, bromine or iodine, in combination with a reducing agent, as catalyst, and wherein nitrogen monoxide is added in a molar amount of 1 to 1000 mol % relative to the amount of nitrogen monoxide present in said catalyst.

28. The process according to claim 27, wherein the reducing agent comprises elemental zinc.

29. The process according to claim 27, wherein the molar amount of added nitrogen monoxide is 10 to 250 mol % relative to the amount of nitrogen monoxide present in said catalyst.

30. The process according to claim 27, wherein the dimerization is conducted at a temperature between 25° C. and 95° C.

31. The process according to claim 27, wherein the reducing agent comprises elemental zinc, the molar amount of added nitrogen monoxide is 10 to 250 mol % relative to the amount of nitrogen monoxide present in said catalyst, and the dimerization is conducted at a temperature between 25° C. and 95° C.

* * * * *